(12) United States Patent
Baggett

(10) Patent No.: US 8,557,874 B2
(45) Date of Patent: Oct. 15, 2013

(54) HEMOSTATIC MATERIAL

(75) Inventor: Richard W. Baggett, Bountiful, UT (US)

(73) Assignee: Epic Wound Care, Inc., Merritt Island, FL (US)

( * ) Notice: Subject to any disclaimer, the term of this patent is extended or adjusted under 35 U.S.C. 154(b) by 710 days.

(21) Appl. No.: 11/945,018

(22) Filed: Nov. 26, 2007

(65) Prior Publication Data

US 2009/0136562 A1  May 28, 2009

(51) Int. Cl.
*A61K 47/00* (2006.01)

(52) U.S. Cl.
USPC ............ 514/781; 514/451; 514/724; 514/506

(58) Field of Classification Search
USPC ........................ 514/451, 772.7, 781, 724, 506
See application file for complete search history.

(56) References Cited

U.S. PATENT DOCUMENTS

| | | | |
|---|---|---|---|
| 4,504,656 A * | 3/1985 | Omiya | 536/66 |
| 4,547,571 A * | 10/1985 | Mukohyama et al. | 536/90 |
| 7,262,181 B2 * | 8/2007 | Zhang et al. | 514/57 |
| 2004/0101548 A1 * | 5/2004 | Pendharkar | 424/445 |
| 2004/0265371 A1 * | 12/2004 | Looney et al. | 424/464 |

\* cited by examiner

*Primary Examiner* — Sreeni Padmanabhan
*Assistant Examiner* — Shobha Kantamneni
(74) *Attorney, Agent, or Firm* — Kirton McConkie; Michael F. Krieger

(57) ABSTRACT

The present invention relates to hemostatic fabric materials, and to the methods for making and using such materials. In particular, the present invention relates to hemostatic fabric materials made from chemically treated cellulose, where the hemostatic material can be soluble on wound surfaces.

11 Claims, 5 Drawing Sheets

HEMOSTATIC MATERIAL

BACKGROUND OF THE INVENTION

1. Field of the Invention

The present invention relates to hemostatic material that is bioabsorbable, which can be fabricated into a variety of forms suitable for use in controlling bleeding from a variety of wounds and to methods for making and using the same.

2. Background and Related Art

Surgical procedures and injuries are often characterized by blood loss. Conventional approaches for dealing with blood loss, such as manual pressure, cauterization, or sutures can be time consuming and are not always effective in controlling bleeding.

A number of topical hemostatic agents have been developed to control bleeding resulting from surgical procedures and injury. Some hemostatic agents, such as collagen-based powders, sponges, and cloths, are of a particulate nature. Particulate hemostatic agents provide a lattice for natural thrombus formation, but are unable to enhance this process in coagulopathic patients. Pharmacologically-active agents, such as thrombin, can be used in combination with a particulate carrier, for example, as in a gel-foam sponge or powder soaked in thrombin, collogen, and/or calcium. Thrombin has been used to control bleeding on diffusely bleeding tissue surfaces, but the lack of a framework onto which the clot can adhere has limited its use. The autologous and allogenic fibrin glues can cause clot formation, but do not adhere well to wet tissue and have little impact on actively bleeding wounds.

Accordingly, a hemostatic fabric material that enhances the process of coagulation is desirable. However, currently known hemostatic fabric materials as used around the world may be insoluble and may have the several other deficiencies. For example, some hemostatic materials may not be used inside the body because absorption may be slow and incomplete. Additionally, some hemostatic materials may require additional medicine to achieve the hemostasis efficacy. Some conventional hemostatic materials may cause pain when the material is removed. Moreover, some current hemostatic materials may slow hemostasis and may interfere with cell regenesis and healing. Therefore, improved hemostasis materials are still needed in modern medical treatments.

Accordingly, a hemostatic material that is bioabsorbable and soluable, which may provide superior hemostasis and that can be fabricated into a variety of forms suitable for use in controlling bleeding from a variety of wounds, is desirable.

SUMMARY OF THE INVENTION

The present invention relates to a hemostatic material that is bioabsorbable, which can be fabricated into a variety of forms suitable for use in controlling bleeding from a variety of wounds and to methods for making and using the same. In particular, the present invention relates to hemostatic fabric materials made from chemically treated plant materials that may be soluble on wound surfaces. The hemostatic materials are suitable for controlling active bleeding and oozing.

In some cases, the hemostatic material may comprise oxidized derivatized esterified cellulose that is based on a beta-(1-4)-D-glucopyranose polymer of cellulose. From polymers of cellulose, oxidized derivatized esterified cellulose may be created through the oxidation of a hydroxyl group on carbon 6 and/or the derivatization of the hydroxyl group on carbon 2, carbon 3, and/or carbon 6 (if carbon 6 is not oxidized) of monomers within the polymer to form one or more acetic acid esters. In some instances, one or more of the acetic acid esters from carbons 2, 3, and/or 6 of the monomers may then be ethoxylated to form an ethyl ester.

The hemostatic material may be soluble both outside and inside the body so the material can be absorbed by the human body. In addition, the material may have several additional advantages. For example, in some instances, no other medicine may be needed in the material, hemostasis may be fast, the material may be easy to carry and store, the material may be stable, the material can meet the requirements of surgery and daily use, the material can be applied for emergent hemostasis in the battle ground, the material may cause no pain and can conform to wounds accurately, the material may stick well until removed, there may be no side effects to the use of the material, and the material may exhibit high hemostasis efficacy-even to patients with a blood-coagulation defect. The hemostatic material of the invention may also be simple, safe, easy to use, economical, can be utilized under any circumstances where hemostasis is needed, and can be made economically in the industry.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

DETAILED DESCRIPTION OF THE INVENTION

Figure 1:
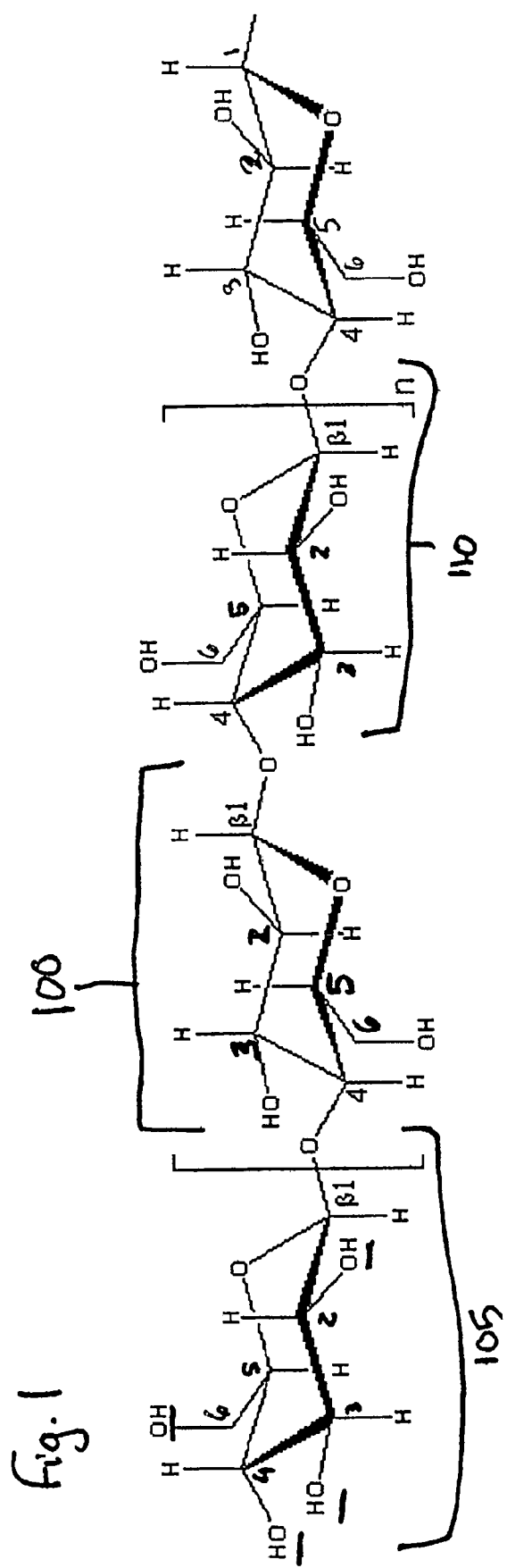
FIG. 1 illustrates some embodiments of the chemical formula of a cellulose polymer.

The present invention relates to a hemostatic material that is bioabsorbable, which can be fabricated into a variety of forms suitable for use in controlling bleeding from a variety of wounds and to methods for making and using the same. In particular, the present invention relates to hemostatic fabric materials made from chemically treated plant materials, such as cellulose, that are soluble on wound surfaces. The hemostatic materials are suitable for controlling active bleeding and oozing from tissues.

1. Hemostasis

To better explain the hemostatic material of the invention, a non-binding description of hemostasis is provided herein. The term hemostasis may be used to refer to the mechanism (e.g., normal vasoconstriction, abnormal obstruction, coagulation, or surgical means) that stems bleeding after injury to the vasculature. Biological hemostasis depends on both cellular components and soluble plasma proteins. In particular, hemostasis by coagulation may be dependent upon a complex interaction of plasma coagulation and fibrinolytic proteins, platelets, and the blood vasculature. The hemostatic process may be conceptually separated into three stages: primary hemostasis, secondary hemostasis, and tertiary hemostasis.

Primary hemostasis may principally be characterized by the formation of a primary platelet plug. The plug may be formed as circulating platelets adhere and aggregate at sites of blood vessel injury. In areas of high shear rate (e.g., microvasculature) aggregation may be mediated by von Willebrand factor (vWf), which may bind to glycoprotein Ib-IX in the platelet membrane. In areas of low shear rate (e.g., arteries) fibrinogen mediates the binding of platelets to the subendothelium by attaching to a platelet receptor. Aggregation begins with platelets adhering to exposed subendothelium. When platelets adhere to the vessel wall they change shape and activate the collagen receptor on their surface to release alpha and dense granule constituents. Injury to the blood vessel wall is additionally followed by vasoconstriction. Vasoconstriction not only retards extravascular blood loss, but also slows local blood flow, enhancing the adherence of platelets to exposed subendothelial surfaces and the activation of the coagulation process.

Formation of the plug may be followed by an aggregation response. Activation of platelets results in exposure of anionic phospholipids that serve as platforms for the assembly of blood coagulation enzyme complexes. Platelet aggregation involves the activation, recruitment, and binding of additional platelets to the adhered platelets. Aggregation is promoted by platelet agonists, such as thromboxane 2, PAF, ADP, and serotonin. Activated platelets synthesize and release thromboxane and platelet activating factor, which are potent platelet aggregating agonists and vasoconstrictors. Activation is enhanced by the generation of another platelet agonist, thrombin, through the coagulation cascade. Platelet aggregation is mediated primarily by fibrinogen, which binds to glycoprotein IIb/IIIa on adjacent platelets. This aggregation leads to the formation of the primary platelet plug, and is stabilized by the formation of fibrin.

Secondary hemostasis may be characterized by fibrin formation through the coagulation cascade, which involves circulating coagulation factors, calcium, and platelets. The coagulation cascade involves three pathways: intrinsic; extrinsic; and common. The main pathway for initiation of coagulation is the extrinsic pathway, while the intrinsic pathway acts to amplify the coagulation cascade.

The extrinsic pathway may involve the tissue factor and factor VII complex, which activates factor X. The extrinsic pathway of blood coagulation is initiated when blood is exposed to tissue factor. Tissue factor, a transmembrane protein, is expressed by endothelial cells, subendothelial tissue and monocytes, with expression being upregulated by cytokines. Tissue factor binds activated factor VII (factor VIIa) and the resulting complex activates factors X and IX. Factor X, in the presence of factor V, calcium, and platelet phospholipid, then activates prothrombin to thrombin. This pathway is rapidly inhibited by a lipoprotein-associated molecule referred to as tissue factor pathway inhibitor. However, the small amount of thrombin generated by this pathway activates factor XI of the intrinsic pathway, which amplifies the coagulation cascade.

Thrombin activates the intrinsic pathway by activation of factors XI and VIII. In the intrinsic pathway activated factor IX (factor IXa) combines with factor VIIIa to provide a second means to activate factor X. The intrinsic pathway involves high-molecular weight kininogen, prekallikrein, and factors XII, XI, IX and VIII. Factor VIII acts as a cofactor (with calcium and platelet phospholipid) for the factor IX-mediated activation of factor X. Activated factor IX, together with activated factor VIII, calcium, and phospholipid, referred to as tenase complex, amplify the activation of factor X, generating large amounts of thrombin.

The extrinsic and intrinsic pathways converge at the activation of factor X. The common pathway involves the factor X-mediated generation of thrombin from prothrombin (facilitated by factor V, calcium and platelet phospholipid), with the production of fibrin from fibrinogen. Factor Xa complexes with factor Va and prothrombin to form prothrombinase, which cleaves prothrombin to generate thrombin, the key enzyme in hemostasis. In the final step of the coagulation cascade, thrombin cleaves fibrinogen to generate fibrin monomers, which then polymerize. This polymer is covalently cross-linked by factor XIIIa (itself generated from factor XIII by thrombin) to form a chemically stable clot. Thrombin also feeds back to activate cofactors V and VIII, thereby further amplifying the coagulation system.

Tertiary hemostasis is characterized by the formation of plasmin, which is the main enzyme responsible for fibrinolysis. At the same time as the coagulation cascade is activated, tissue plasminogen activator is released from endothelial cells. Tissue plasminogen activator binds to plasminogen within the clot, converting it into plasmin. Plasmin lyses both fibrinogen and fibrin in the clot, releasing fibrin and fibrinogen degradation products.

Finally, fibrin is digested by the fibrinolytic system, the major components of which are plasminogen and tissue-type plasminogen activator (tPA). Both of these proteins are incorporated into polymerizing fibrin, where they interact to generate plasmin, which, in turn, acts on fibrin to dissolve the preformed clot.

The fibrinolytic system is, in turn, regulated by three serine proteinase inhibitors, namely, antiplasmin, plasminogen activator inhibitor-1 (PAI-1), and plasminogen activator inhibitor-2 (PAI-2). Plasma D-dimers are generated when the endogenous fibrinolytic system degrades fibrin. They consist of two identical subunits derived from two fibrin molecules. Unlike fibrinogen degradation products, which are derived from fibrinogen and fibrin, D-dimers are a specific cross-linked fibrin derivative The process of fibrin deposition is limited by mechanisms of the natural anticoagulant system. The maintenance of adequate blood flow and the regulation of cell surface activity limit the local accumulation of activated blood coagulation enzymes and complexes. Antithrombin (AT) is a plasma protein member of the serpin (serine protease inhibitor) family that inhibits the activities of all of the activated coagulation enzymes. The inhibitory effect of AT is increased several thousand-fold by binding to heparin. Protein C is a vitamin K-dependent protein that proteolyses factor Va and factor VIIIa to inactive fragments. Protein C binds to an endothelial cell protein C receptor (EPCR) and is activated by thrombin bound to thrombomodulin, another endothelial cell membrane-based protein, in a reaction that is modulated by a cofactor, protein S. Tissue factor pathway inhibitor is a lipoprotein-associated plasma protein that forms a quaternary complex with tissue factor, factor VIIa, and factor X, thereby inhibiting the extrinsic coagulation pathway.

2. Hemostatic Mechanism

The following is a description of the ways in which the hemostatic material of the invention may contribute to achieving hemostasis:

a) Hemostasis Through Physical Path

When the hemostatic material contacts blood, the hemostatic material may stimulate a blood clotting cascade. For example, the hemostatic material may absorb a large quantity of fluid (e.g., lymph or water) and thereby increase the concentration and viscosity of the blood to slow the flow of the blood. Meanwhile, soluble hemostatic material may cover the wound surfaces and expand after it absorbs fluid. As the material contacts fluid in the blood, some part of the material may be dissolved to form a viscous body and clog the end of capillary blood vessels.

b) Hemostasis Through Chemical Path

The term "Hemostasis through chemical path" means that when soluble hemostatic material in the invention contacts platelets, absorption and coagulation may occur at an increased rate.

c) Hemostasis Through Physiology Path

The term "Hemostasis through physiology path" means that the hemostatic material of this invention can activate the coagulation factors in the human body and boost the formation of thrombin so as to generate hemostasis efficacy. Coagulation factor may be the key factor to activate the endogenous coagulation system as well as the external coagulation system. It is already known that some coagulation factors may bring positive electricity; therefore, they could be generally activated by a substance with negative electricity. Because the hemostatic material may be water-soluble, it can generate large quantities of negative electricity after it is dissolved in water to activate the coagulation factors.

3. Hemostatic Material

The preferred embodiments provide compositions and materials that react with the hemostatic system to treat or prevent bleeding. In particular, the compositions and materials of preferred embodiments may result in coagulation of blood. Effective delivery of hemostatic agents to wounds is desirable in the treatment of injuries characterized by bleeding, as well as in surgical procedures where the control of bleeding can become problematic (e.g., surgical procedures involving large surface areas, heavy arterial or venous bleeding, oozing wounds, organ laceration/resectioning, etc.). The compositions and materials of preferred embodiments can possess a number of advantages in delivery of hemostatic agents to wounds, including, but not limited to, ease of application and removal, bioadsorption potential, antigenicity, and tissue reactivity.

Depending upon the nature of the wound and the treatment method employed, the devices of preferred embodiments of the hemostatic material can be fabricated in various forms. For example, a puff, fleece, gel, powder, or sponge form can be preferable for controlling the active bleeding from an artery or vein, or for controlling internal bleeding during laparoscopic procedures. In neurosurgery, where oozing brain wounds are commonly encountered, a sheet or towel form of the hemostatic material can be preferred. Likewise, in oncological surgery, especially of the liver, it can be preferred to employ a sheet form or sponge form of the hemostatic material, which may be placed in or on the tumor bed to control oozing. In dermatological applications, a sheet form can be preferred. In closing punctures in a blood vessel, a puff or fleece form may generally be preferred. A suture form, especially a microsuture form, can be preferred in certain applications. Despite differences in delivery and handling characteristics of the various forms, the devices may each be effective in deploying hemostatic agents to an affected site and rapidly initiating hemostatic plug formation through platelet adhesion, platelet activation, and/or blood coagulation.

The hemostatic material of the invention may be formed from any appropriate material. For instance, some non-limiting examples of materials that may be used to produce the hemostatic material may include cellulose, cellulose derivatives (e.g. alkyl cellulose (e.g., methyl cellulose), hydroxyalkyl cellulose, alkylhydroxyalkyl cellulose, cellulose sulfate, salts of carboxymethyl cellulose, carboxymethyl cellulose, and carboxyethyl cellulose), chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, heparin, heparin sulfate, heparan, heparan sulfate, dermatan sulfate, keratin sulfate, carrageenans, chitosan, starch, amylose, amylopectin, poly-N-glucosamine, polymannuronic acid, polyglucuronic acid, polyguluronic acid and derivatives of the above.

According to some embodiments, however, the described hemostatic material may comprise a compound that may be based on a beta-(1-4)-D-glucopyranose polymer of cellulose, as is illustrated in FIG. 1. In particular, FIG. 1 illustrates that a beta-linked glucopyranose residue 100, which is connected to two other glucopyranose residues (e.g., residues 105 and 110) in a $^4C_1$ chair configuration, may comprise a hydroxyl group that is bound to carbon 2, carbon 3, and carbon 6.

In some embodiments, the hemostatic material may comprise oxidized derivatized esterified cellulose. According to some embodiments, the hemostatic material comprising oxidized derivatized esterified cellulose may be created from beta-(1-4)-D-glucopyranose polymers through the oxidation of the hydroxyl group on carbon 6 and/or the derivatization of the hydroxyl group on carbon 2, carbon 3, and/or carbon 6 (if carbon 6 is not oxidized) to form one or more acetic acid esters. According to some embodiments, one or more of the acetic acid esters from carbons 2, 3, and/or 6 may then be ethoxylated to form an ethyl ester.

Figure 2:
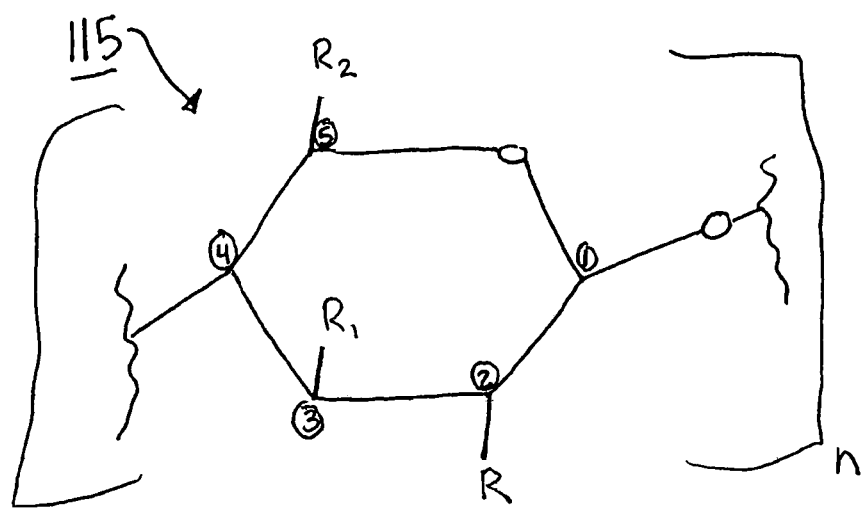
FIG. 2 illustrates some embodiments of the chemical formula of a monomer that may be used to form polymers of the hemostatic material of the invention.

FIG. 2 illustrates some embodiments of the structural formula of a basic unit, or a monomer, of oxidized derivatized esterified cellulose that may be used to create polymers of the hemostatic material. Specifically, FIG. 2 shows that a six-membered glucopyranosyl ring 115 that serves as a monomer of the hemostatic material may comprise a variety of functional groups. For example, FIG. 2 illustrates that a first functional group R may be bound to the ring 115 through carbon 2, a second functional group $R_1$ may be bound to the ring 115 through carbon 3, and/or a third functional group $R_2$ may be bound to the ring 115 through carbon 5.

The various functional groups, including R, $R_1$, and $R_2$, may comprise any functional group that allows the hemostatic material to be bioabsorbable and to reduce bleeding in a wound. For instance, R, $R_1$, and/or $R_2$ may each individually comprise —$CH_2OCH_2(COO)CH_xCH_x$, —$(COO)CH_xCH_x$, —$OCH_2(COO)CH_xCH_x$, —OH, —$CH_2OH$, or COOH. However, according to some preferred embodiments, R may comprise —OH or an ethyl carboxymethyl group, such as —$OCH_2(COO)CH_2CH_3$. In some preferred embodiments, $R_1$ may comprise —OH or an ethyl carboxymethyl group, such as —$OCH_2(COO)CH_2CH_3$. Moreover, in some preferred embodiments, $R_2$ may comprise an ethyl carboxymethyl group, such as —CH$_2$OCH$_2$(COO)CH$_2$CH$_3$, or a carboxyethyl group, such as —(COO)CH$_2$CH$_3$.

Figure 3:
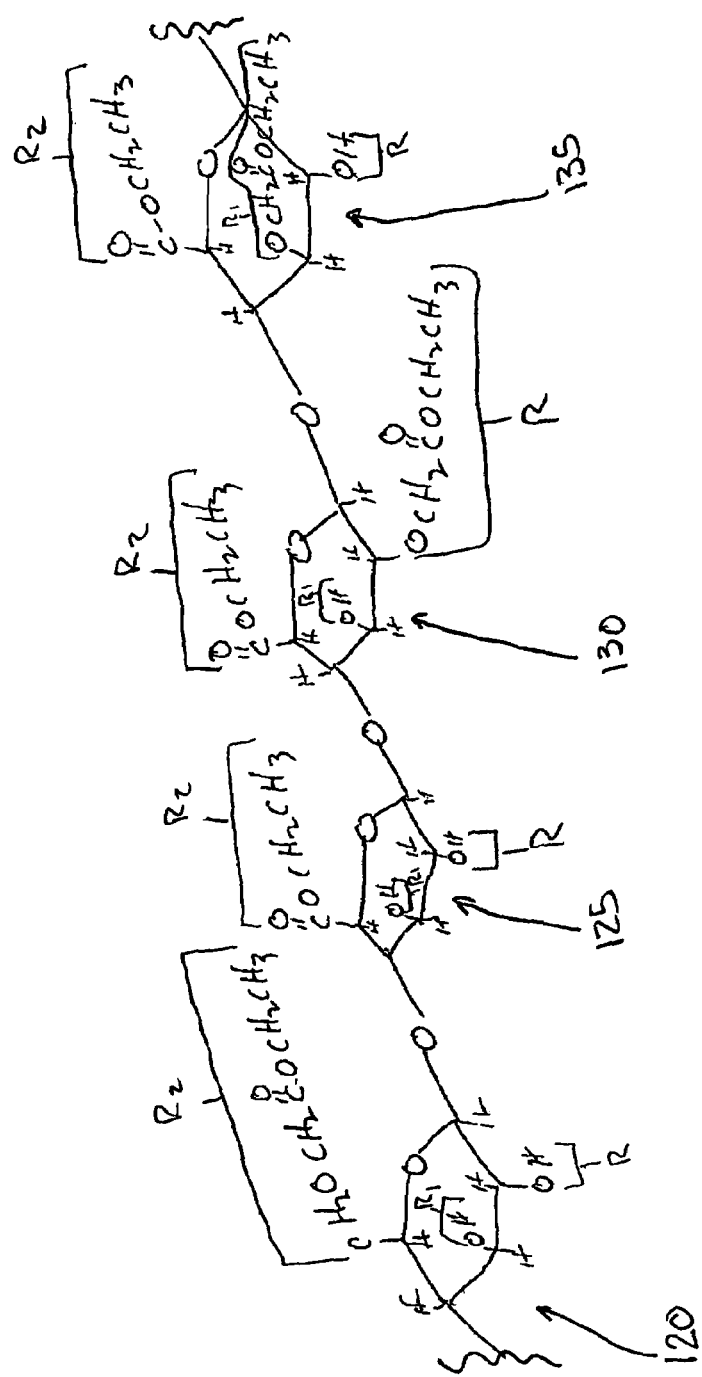
FIG. 3 illustrates some embodiments of the chemical formula of a portion of a polymer that may be used in the hemostatic material of the invention.

A monomer used to form polymers of the hemostatic material may have any suitable combination of functional groups that allows the hemostatic material to comprise polymers of oxidized derivatized esterified cellulose, and not solely unreacted cellulose. For instance, FIG. 3 illustrates some embodiments of a portion of a polymer of oxidized derivatized esterified cellulose. Namely, FIG. 3 illustrates several non-limiting examples of monomers connected together, wherein each monomer comprises a different combination of functional groups. For example, FIG. 3 illustrates that in a first monomer 120, R may comprise —OH, R1 may comprise —OH, and R$_2$ may comprise —CH$_2$OCH$_2$(COO)CH$_2$CH$_3$. FIG. 3 also shows that in a second monomer 125, R may comprise —OH, R$_1$ may comprise —OH, and R$_2$ may comprise —(COO)CH$_2$CH$_3$. Further, FIG. 3 depicts that in a third monomer 130, R may comprise —OCH$_2$(COO)CH$_2$CH$_3$, R$_1$ may comprise —OH, and R$_2$ may comprise —(COO)CH$_2$CH$_3$. Finally, FIG. 3 shows that in a fourth monomer 135, R may comprise —OH, R$_1$ may comprise —OCH$_2$(COO)CH$_2$CH$_3$, and R$_2$ may comprise —(COO)CH$_2$CH$_3$.

Figure 4:
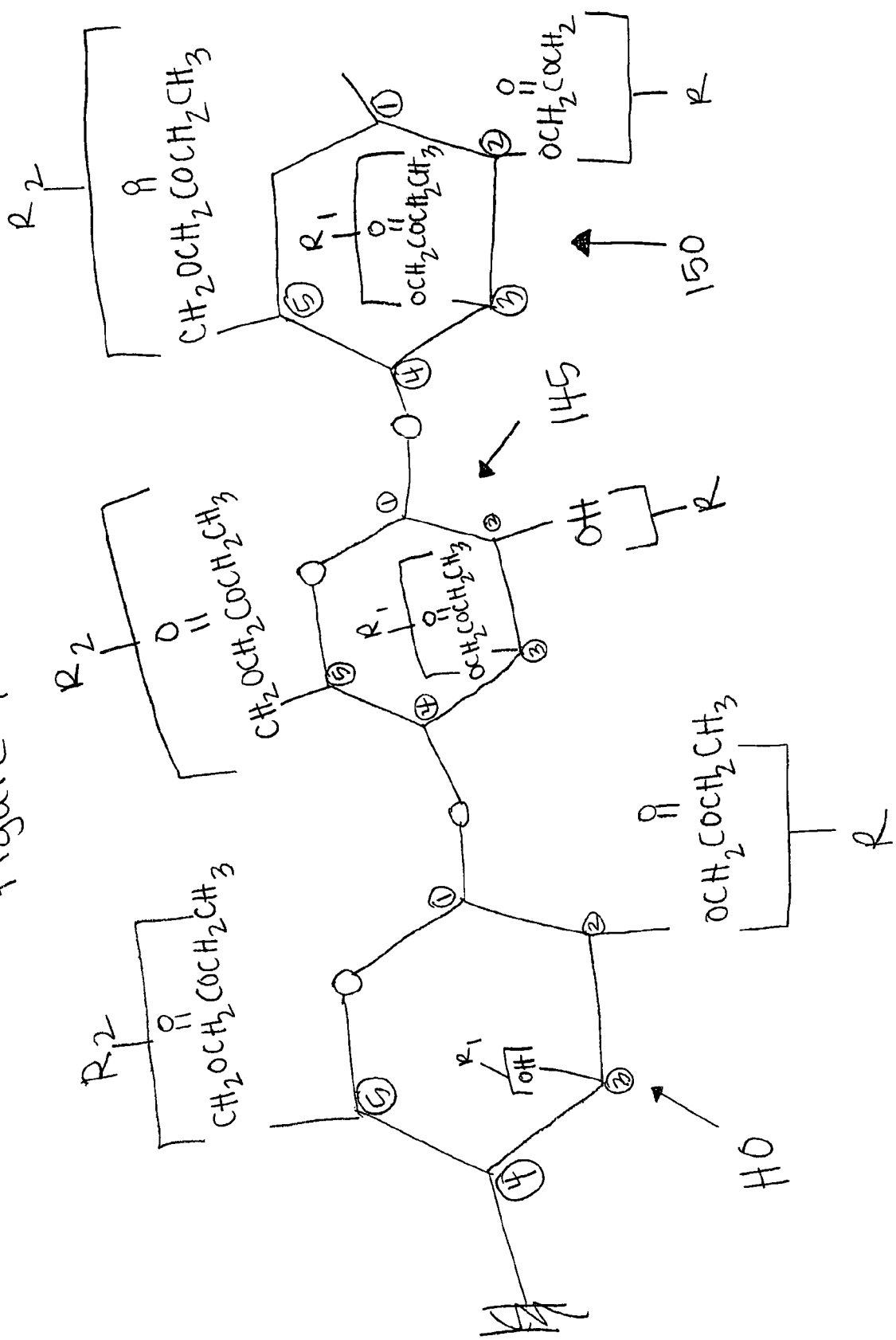
FIG. 4 illustrates some embodiments of the chemical formula of a portion of a polymer that may be used in the hemostatic material of the invention.
Figure 5:
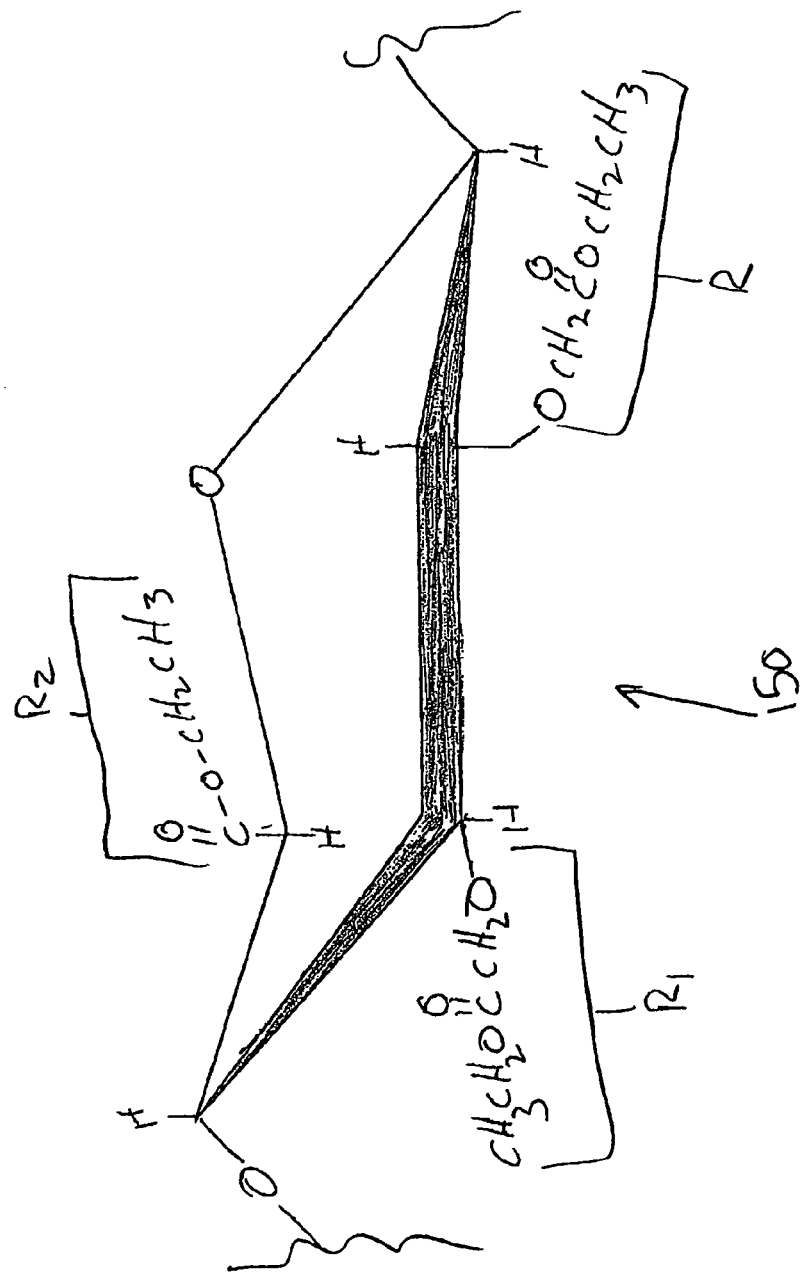
FIG. 5 illustrates some embodiments of the chemical formula of a monomer that may be used to form polymers of the hemostatic material of the invention.

According to some embodiments, FIGS. 4 and 5 illustrate several additional monomers that show other non-limiting examples of functional group combinations that may be possible in a polymer of oxidized derivatized esterified cellulose that is used to form the hemostatic material. Specifically, FIG. 4 shows that in a fifth example of a monomer 140, R may comprise —OCH$_2$(COO)CH$_2$CH$_3$, R$_1$ may comprise —OH, and R$_2$ may comprise —CH$_2$OCH$_2$(COO)CH$_2$CH$_3$. FIG. 4 illustrates that in a sixth example of a monomer 145, R may comprise —OH, R$_1$ may comprise —OCH$_2$(COO)CH$_2$CH$_3$, and R$_2$ may comprise —CH$_2$OCH$_2$(COO)CH$_2$CH$_3$. Also, FIG. 4 depicts a seventh example of a monomer 150 that shows that R may comprise —OCH$_2$(COO)CH$_2$CH$_3$, R$_1$ may comprise —OCH$_2$(COO)CH$_2$CH$_3$, and R$_2$ may comprise —CH$_2$OCH$_2$(COO)CH$_2$CH$_3$. Moreover, FIG. 5 illustrates an eighth non-limiting example of a monomer 150, where the monomer 150 is depicted in a chair configuration. FIG. 5 shows that, in some embodiments, R may comprise —OCH$_2$(COO)CH$_2$CH$_3$, R$_1$ may comprise —OCH$_2$(COO)CH$_2$CH$_3$, and R$_2$ may comprise —(COO)CH$_2$CH$_3$.

A polymer of oxidized derivatized esterified cellulose may comprise any combination of monomers that comprise any suitable combination of the aforementioned functional groups. Thus, a monomer with any combination of functional groups may be connected to one or two other monomers with the same or different functional groups located on the same and/or different carbons. For example, FIG. 3 depicts one possible combination of monomers (i.e., monomers 120, 125, 130, and 135) in a portion of a polymer of the hemostatic material. Nevertheless, in other embodiments, monomers with different or similar combinations of functional groups may be connected throughout a polymer of the hemostatic material in any other order that is chemically feasible.

Polymers of the oxidized derivatized esterified cellulose may be any suitable length that allows the polymers to be used to control bleeding. For example, FIG. 2 illustrates that a polymer of oxidized derivatized esterified cellulose may comprise any suitable number of monomers, where the number of monomers is referred to as n. Indeed, in some embodiments, a polymer of oxidized derivatized esterified cellulose may comprise between about 2 and about 150,000 monomers. In other embodiments, however, a polymer may comprise between about 2 and about 20,000 monomers. In still other embodiments, a polymer may comprise between about 500 and about 2,000 monomers. Indeed, in a preferred embodiment, a polymer may comprise about 1000 monomers.

According to some embodiments, the monomers and other compounds may have asymmetric centers. Unless otherwise indicated, all chiral, diastereomeric, and racemic forms of the described monomers and all geometric isomeric forms of the described monomers may be included in the present invention. It will also be appreciated that compounds of the present invention that contain asymmetrically substituted carbon atoms may be isolated in optically active or racemic forms. Furthermore, this invention may encompass any or all intermediate products and byproducts that may be present in the formation of the described oxidized derivatized esterified cellulose. For instance, while in some embodiments, a polymer may be about 99.99% ethoxylated, this invention may comprise polymers that are ethoxylated to higher or lower degrees. Additionally, this invention may also encompass monomers that are connected to other monomers through various forms of ether bonds, which may include beta and/or alpha bonds.

As mentioned, the hemostatic material may be soluble and may be made by the chemical treatment of plant fiber, such as cellulose. The untreated plant fiber can absorb water, but may be insoluble. After being treated by the process of the invention, its physical and chemical properties may be changed significantly so that the resulting hemostatic material is soluble in water and body fluids. As mentioned the hemostatic material of the invention can be used both inside and outside the body to stop bleeding. When utilized in biological systems the soluble hemostatic material of this invention may absorb water and expand. This absorption may then allow the structure of the hemostatic material to be dismantled and change to a kind of transparent gel. Finally, the material may dissolve completely. The hemostatic material of the invention may increase hemostatic efficacy by at least three mechanisms: physical, chemical, and physiological; each of which are discussed below at greater length. In particular, the hemostatic material may activate the blood-coagulation factors to boost the formation of thrombin, and the material may absorb fluid from the blood and expand to form a colloid. Application of the hemostatic material may increase the viscosity of blood, blood flow speed may be reduced, and the colloid may clog the opening of the blood vessel through which bleeding is taking place. Because the soluble hemostatic material may activate the blood-coagulation factors and boost the formation of thrombin, it may notably be effective for patients with blood-coagulation obstructions or defects.

The hemostatic material can be provided in the form of a sheet of a pre-selected size. Alternatively, a larger sheet of the hemostatic material can be cut or trimmed to provide a size and shape appropriate to the wound. Although the hemostatic material may be bioabsorbable, in cutaneous or topical applications it may preferably be removed from the wound after a satisfactory degree of hemostasis has been achieved. When the hemostatic fabric is employed in internal applications, it may preferably be left in place to be absorbed by the body over time. Such hemostatic fabrics may be particularly well suited for use in the treatment of oozing wounds.

The soluble hemostatic material can be used both for a broad range of uses, including clinical and for first aid. It can advantageously and easily be use in hostile environments where a simple and effective means for stopping the flow of blood or body fluids is desired (e.g., battleground situations). The hemostatic material may be soluble and may be used in the form of a fabric material, such as a gauze material, and can be used on wound surfaces under pressure. The material can be provided free of any medications, if desired, or may contain desired medications for particular purposes.

The hemostatic material may suitable for use in both surgical applications as well as for use in field treatment of traumatic injuries. For example, the material may be suitable for use in vascular surgery, where bleeding can be particularly problematic. The hemostatic material may be suitable for use in cardiac surgery, where multiple vascular anastomoses and cannulation sites, complicated by coagulopathy induced by extracorporeal bypass, can result in bleeding that can only be controlled by topical hemostats. The hemostatic material may be suitable to produce rapid and effective hemostasis during spinal surgery, where control of osseous, epidural, and/or subdural bleeding or bleeding from the spinal cord is not amenable to sutures or cautery. In such instances, the hemostatic material can minimize the potential for injury to nerve roots and reduce the procedure time. In another example, the hemostatic material may also be suitable for use in liver surgery, in live donor liver transplant procedures, or in the removal of cancerous tumors; where there is a substantial risk of massive bleeding. The material may be suitable for use as an effective hemostatic material, which can significantly enhance patient outcome in such procedures. Even in situations where massive bleeding is not a problem, the hemostatic material may be suitable for use to achieve hemostasis. For example, the material may be used in dental procedures, such as tooth extractions; for abrasions; burns; sports related injuries, and the like. The material may also be suitable for use in neurosurgery, where oozing wounds are common and are difficult to treat.

The nature of the hemostatic material of this invention may include any combination of the following attributes:

a) Water-Solubility

The known prior art cellulose fiber materials may contain hydrophilic hydroxyamino-. However, in such cellulose fiber materials large quantities of hydrogen bonds may exist among the molecules and the degree of crystallinity may be high. Thus, the known prior art cellulose fiber material may not be dissolved in water. Nevertheless, during the processing according to the invention, the cellulose may be chemically changed so that:

i) The degree of polymerization may be decreased, as well as the dispersion force and inductive capacity.

ii) Hydrophilic radical groups may be induced to widen the space between the molecules and destroy the hydrogen bonds inside and/between some of the molecules.

iii) The degree of crystallinity may be decreased, the amorphism zone may be enlarged, orientation forces between molecules may be decreased, and it is possible that water molecules may form molecular compounds in tiny packs.

From the point of view of thermodynamics, the free energy of mixing between the molecules of the hemostatic material and water molecules may be below zero. Furthermore, because the solubility difference may also be less than about 1.7 to about 2.0, dissolution may occur. As mentioned, the dissolution process of the described hemostatic material by water may include: the hemostatic material absorbing fluid and expanding, the unbinding of the structure so the material may be transformed to a transparent gel, and dissolving the material completely.

b) Absorbability to Water and Polarizable Medium

If the speed of absorption of the hemostatic material to water and polarizable medium is high, the amount of absorption may be large. This can be helpful for hemostasis.

4. Method for Making Soluble Hemostatic Material

The formation of the soluble hemostatic material comprised of oxidized derivatized esterified cellulose may be accomplished in any suitable manner. Nevertheless, in order to provide a better understanding of the soluble hemostatic material and its methods of production, a non-limiting example of a typical method of making the hemostatic material is provided below, wherein the method may comprise:

a) Placing sodium hydroxide, sodium carbonate, sodium hypochlorite in to the internal bladder of a reaction vessel, then adding in an appropriate amount of pure water and stirring until the ingredients are dissolved. Pouring ethyl alcohol (preferably about 95% ethyl alcohol) in to solution in the internal bladder and mixing. Turning on a heater and keeping the temperature of the internal bladder above 20° C. (preferably between about 25° C. and about 28° C.) and holding at the desired temperature for a period of time, preferably for about 10 hours.

b) Placing the raw material (e.g., cellulose) to be chemically treated, preferably degreased and bleached plant fiber in the form of gauze into the mixed solution in the reaction vessel. Maintaining the temperature of the external body above 20° C., preferably near about 30° C.±3° C. Moreover, the method may comprise maintaining the temperature of the internal bladder between about 20° C. and about 30° C., and preferably at about 26° C.±1° C.

c) Decreasing the temperature of the internal bladder to about 20° C.±3° C., and beginning to rotate the reaction vessel for a period of time, preferably about five hours.

d) Allowing cold water to move into the internal bladder so that after a period of time, the temperature may drop to below 20° C., and preferably to about 5° C.±3° C. Allow the solution to react at this decreased temperature for a period of time, preferably about one hour.

e) Adding an appropriate amount of alcohol, preferably 95% ethyl alcohol, and an appropriate amount of chloroacetic acid, into the reaction vessel. After 30 minutes, the temperature in the internal bladder may increase up to a temperature above 20° C., preferably the temperature will move from about 5° C.±3° C. to about 41° C.±3° C. Add an appropriate amount of hydrogen peroxide. Decrease the temperature below 40° C., preferably to about 32° C.±3° C., and allow the reaction to continue for a period of time, preferably about 1.5 hours.

f) Put the material from the reaction vessel into a container, preferably a stainless-steel tub. Add an appropriate amount of alcohol, preferably 70% ethyl alcohol, stir and rise. At that point, dry it up, preferably by centrifugal dewatering.

g) Put the material obtained as above into another container, preferably made of stainless steel, with an appropriate amount of a selected alcohol, preferably 70% ethyl alcohol, then counteract it by adding an acid, preferably Hydrochloric acid, to solution to achieve the desired pH value, preferably a pH value of about 7±0.5.

h) Take out the material and allow it to dry. Preferably one would treat the material one more time or many times as described as above in another container until the solution becomes clear. Allow the material to dry. Optionally one may iron the material to make it flat.

5. Use of Additional Hemostatic Agents

Other suitable hemostatic agents that can be employed in preferred embodiments may include, but are not limited to, clotting factor concentrates, recombinant Factor VIIa, alphanate FVIII concentrate, bioclate FVIII concentrate, monoclate-P FVIII concentrate, haemate P FVIII, von Willebrand factor concentrate, helixate FVIII concentrate, hemophil-M FVIII concentrate, humate-P FVIII concentrate, hyate-C®. Porcine FVIII concentrate, koate HP FVIII concentrate, kogenate FVIII concentrate, recombinate FVIII concentrate, mononine FIX concentrate, and fibrogammin P FXIII concentrate. Such hemostatic agents can be applied to the hemostatic material of this invention in any suitable form (e.g., as a powder, as a liquid, in a pure form, in a suitable excipient, on a suitable support or carrier, or the like).

A single hemostatic agent or combination of hemostatic agents can be employed. Preferred loading levels for the hemostatic agent on the hemostatic material can vary, depending upon, for example, the nature of the selected material and hemostatic agent, the form of the material, and the nature of the wound to be treated. However, in general in the case of hemostatic gauze, a generally preferred weight ratio of hemostatic agent to hemostatic gauze may be from about 0.001:1 or lower to about 2:1 or higher. More preferably, a weight ratio of additional hemostatic agent to hemostatic material may be from about 0.05:1 or lower to about 2:1 or higher. More preferably, a weight ratio from about 0.06:1, 0.07:1, 0.08:1, 0.09:1, 0.10:1, 0.15:1, 0.20:1, 0.25:1, 0.30:1, 0.35, 0.40:1, 0.45:1, 0.50:1, 0.55:1, 0.60:1, 0.65:1, 0.70:1, 0.75:1, 0.80:1, 0.85:1, 0.90:1, or 0.95:1 to about 1:1, 1.1:1, 1.2:1, 1.3:1, 1.4:1, or 1.5:1 may be employed, although higher or lower ratios can be preferred for certain embodiments.

6 Use of Auxiliary Substances in Preparing Hemostatic Materials

In certain embodiments, it can be desirable to utilize the hemostatic material comprising the described oxidized derivatized esterified cellulose alone as the hemostatic material. However, in other embodiments, other materials such as collagen, natural cotton cellulose, pure plant fiber, silk, rayon, or nylon may be used in conjunction with the described oxidized derivatized esterified cellulose as a hemostatic material. Other substances that can be utilized in conjunction with the described oxidized derivatized esterified cellulose may include thrombin, fibrinogen, hydrogels, and oxidized cellulose. Other auxiliary substances can also be employed, as will be appreciated by one skilled in the art.

7. Multifunctional Hemostatic Materials

In addition to effectively delivering a hemostatic agent to a wound, in some embodiments, the hemostatic materials comprising oxidized derivatized esterified cellulose can deliver other substances as well. In a particularly preferred embodiment, such substances may include medicaments, pharmaceutical compositions, therapeutic agents, and/or other substances producing a physiological effect. The substances can be deposited on the hemostatic material by any suitable method known in the art for depositing a material onto another material or incorporating an agent into a material.

In some embodiments, any suitable medicament, pharmaceutical composition, therapeutic agent, or other desirable substance can be incorporated into the hemostatic material comprising the described oxidized derivatized esterified cellulose. Preferred medicaments may include, but are not limited to, anti-inflammatory agents, anti-infective agents, anesthetics, immunosuppressive agents and chemotherapy agents.

Some non-limiting examples of suitable anti-inflammatory agents may include, but are not limited to, nonsteroidal anti-inflammatory drugs (NSAIDs), such as aspirin, celecoxib, choline magnesium trisalicylate, diclofenac potasium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids, such as cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinonide, betamethasone dipropionate, betamethasone valerate, desonide, desoximetasone, fluocinolone, triamcinolone, clobetasol propionate, and dexamethasone.

Anti-infective agents may include, but are not limited to, anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin, clindamycin, colistimethate sodium, polymyxin b sulfate, vancomycin, antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones (ciprofloxacin, levofloxacin), sulfonamides (sulfadiazine, sulfisoxazole), sulfones (dapsone), furazolidone, metronidazole, pentamidine, sulfanilamidum crystallinum, gatifloxacin, and sulfamethoxazole/trimethoprim.

Anesthetics can include, but are not limited to, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocalne, and phenazopyridine.

Chemotherapy agents may include, but are not limited to, adriamycin, alkeran, Ara-C, BiCNU, busulfan, CCNU, carboplatinum, cisplatinum, cytoxan, daunorubicin, DTIC, 5-FU, fludarabine, hydrea, idarubicin, ifosfamide, methotrexate, mithramycin, mitomycin, mitoxantrone, nitrogen mustard, taxol, velban, vincristine, VP-16, gemcitabine (gemzar), herceptin, irinotecan (camptosar, CPT-11), leustatin, navelbine, rituxan, STI-571, taxotere, topotecan (hycamtin), xeloda (capecitabine), and zevelin.

A variety of other medicaments and pharmaceutical compositions may also be suitable for use in preferred embodiments of the hemostatic material comprising oxidized derivatized esterified cellulose. These may include cell proliferative agents, such as tretinoin; procoagulants, such as dencichine (2-amino-3-(oxalylamino)-propionic acid); and sunscreens, such as oxybenzone and octocrylene.

Human epidermal growth factor (hEGF) can also be preferred for certain embodiments. This small molecular weight peptide is a mitogenic protein and may be critical for skin and epidermal regeneration. It may be a small 53 amino acid residue long protein with 3 disulfide bridges. The epidermal growth factor can be used as produced, or can be polymerized prior to use in preferred embodiments. Presence of hEGF can have a positive effect upon skin healing and regeneration.

Other substances which can be used in preferred embodiments can include, or be derived from, traditional medicaments, agents, and remedies that have known antiseptic, wound healing, and pain relieving properties. These agents may include, but are not limited to, Sanqi (Radix Notoginsent). Another such agent may be Dahuang (Radix Et Rhizoma Rhei). One of its compounds, Emodin, may cause anti-inflammatory effects and can also effectively reduce soft tissue edema. Another agent may include Zihuaddng (Herba Violae), which has been used as an antibiotic agent.

Baiji (Rhizoma Bletillae) has been used as a hemostatic agent and also to promote wound healing for years. It may contain the following substances: (3,3'-di-hydroxy-2', 6'-bis (p-hydroxybenzyl)-5-methoxybibenzy-1); 2,6-bis(p-hydroxybenzyl)-3', 5-dimethoxy-3-hydroxy-bibenzyl); (3,3'-dihydroxy-5-methoxy-2,5',6-tris(p-hydroxy-benzyl) bibenzyl; 7-dihydroxy-1-p-hydroxybenzyl-2-methoxy-9,10-dihydro-phenanthrene); (4,7-dihydroxy-2-methoxy-9, 10-dihydroxyphenanthrene); Blestriarene A (4,4'-dimethoxy-9,9', 10,10'-tetrahydro[1,1'-biphenanthrene]-2,2',7,7'-te-trol); Blestriarene B (4,4'-dimethoxy-9, 10-dihydro[1,1'-biphenanthrene]-2-,2',7,7'-tetrol); Batatasin; 3'-O-Methyl Batatasin; Blestrin A(1); Blestrin B(2); Blestrianol A (4,4'-dimethoxy-9,9',10,10'-tetrahydro]-1',3-1-biphenanthrene]-2,2',7,7'-tetraol); Blestranol B (4',5-dimethoxy-8-(4-hyd-roxybenzyl)-9, 9',10,10'-tetrahydro-[1',3-biphenanthrene]-2,2',7,7'-tetraol-Blestranol C (4',5'-dimethoxy-8-(4-hydroxybenzyl)-9,10-dihydro-[1',3-bi-phenanthrene]-2,2',7,7'-tetraol); (1,8-bi(4-hydroxybenzyl)-4-methoxy-phena-nthrene-2,7-diol); 3-(4-hydroxybenzyl)-4-methoxy-9,10-dihydro-phenanthrene--2, 7-diol; (1,6-bi(4-hydroxybenzyl)-4-methoxy-9,10-dihydro-phenanthrene-2,-7-diol; (1-p-hydroxybenzyl-4-methoxyphenanthrene-2,7-diol); 2,4,7-trimethoxy-phenanthrene; 2,4,7-trimethoxy-9,10-dihydrophenanthrene; 2,3,4,7-tetramethoxyphenanthrene; 3,3',5-trimethoxy-bibenzyl; 3,5-dimethoxybibenzyl; and Physcion.

Rougui (Cortex Cinnamoni) has pain relief effects. It may contain some or all of the following substances: anhydrocinnzeylanine; anhydrocinnzeylanol; cinncassiol A; cinnacassiol A monoacetate; cinncassiol A glucoside; cinnzeylanine; cinnzeylanol; cinncassiol B glucoside; cinncassiol C.sub.1; cinncassiol C.sub.1 glucoside; cinncassiol C.sub.2; cinncassiol C.sub.2; cinncassiol D.sub.1; cinncassiol D.sub.1 glucoside; cinncassiol D.sub.2; cinncassiol D.sub.2 glucoside; cinncassiol D.sub.3; cinncassiol D.sub.4; cinncassiol D.sub.4 glucoside; cinncassiol E; lyoniresinol; 3.alpha.—O—B-D-glucopyranoside; 3,4,5-trimethoxyphenyl 1-O-.beta.-D-apiofuranosyl-(1.fwdarw.6)-.beta.-D-glucopyranoside; (.+-.)-syringaresinol; cinnamic aldehyde cyclic glycerol 1,3 acetals; epicatechin; 3'-O-methyl-(−)-epicatechin; 5,3'-di-O-methyl-(−)-epicatechin-; 5,7,3'-tri-O-methyl-(−)-epicatechin, 5'-O-methyl-(+)-catechin; 7,4'-di-O-methyl-(+)-catechin; 5,7,4'-tri-O-methyl-(+)-catechin; (−)-epicatechin-3-O-.beta.-D-glucopyranoside; (−)-epicatechin-8-C-.beta.-D-glucopyranoside; (−)-epicatechin-6-C-.beta.-D-glucopyranoside; procyanidin; cinnamtannin A.sub.2, A.sub.3, A.sub.4; (−)-epicatechin; procyanidins B-1, B-2, B-5, B-7, C-1; proanthocyanidin; proanthocyanidin A-2; 8-C-.beta.-D-glucopyranoside; procyanidin B-2 8-C-.beta.-D-glycopyranoside; cassioside [(4s)-2,4-dimethyl-3-(4-hydroxy—3-hydroxymethyl-1-butenyl)-4-(.beta.-D-glucopyranosyl) methyl-2-cyclohexen-1-one]; 3,4,5-trimethoxyphenyl-.beta.-D-apiofuranosyl-[(1.f-wdarw.6)-.beta.-D-glucopyranoside; coumarin; cinnamic acid; procyanidin; procyanidin B.sub.2; cinnamoside[(3R)-4-{(2'R,4' S)-2'-hydroxy-4'-(.beta.-1-D-apiofuranoxy-(1.fwdarw.6)-.beta.-D-glucopyranosyl)-2',6',6'-trimethyl-cyclohexylidene}-3-buten-2-one]; cinnamaldehyde; 3-2(hydroxyphenyl)-propano-ic acid; O-glucoside; cinnaman A.sub.2; P, S, Cl, K, Ca, Ti, Mn, Fe, Cu, Zn, Br, Rb, Sr, and Ba.

Other substances that can be incorporated into the hemostatic material of preferred embodiments may include various pharmacological agents, excipients, and other substances well known in the art of pharmaceutical formulations. Other pharmacological agents may include, but are not limited to, antiplatelet agents, anticoagulants, ACE inhibitors, and cytotoxic agents. These other substances can include ionic and nonionic surfactants (e.g., Pluronic™, Triton™), detergents (e.g., polyoxyl stearate, sodium lauryl sulfate), emulsifiers, demulsifiers, stabilizers, aqueous and oleaginous carriers (e.g., white petrolatum, isopropyl myristate, lanolin, lanolin alcohols, mineral oil, sorbitan monooleate, propylene glycol, cetylstearyl alcohol), emollients, solvents, preservatives (e.g., methylparaben, propylparaben, benzyl alcohol, ethylene diamine tetraacetate salts), thickeners (e.g., pullulin, xanthan, polyvinylpyrrolidone, carboxymethylcellulose), plasticizers (e.g., glycerol, polyethylene glycol), antioxidants (e.g., vitamin E, vitamin K, vitamin C, calcium), buffering agents, flexible agents (e.g., silicon), antibiotics, low-grade antibiotics (e.g., silver, tetracycline, etc.), and the like.

8. Alternative Forms of Hemostatic Materials

While it is generally preferred to apply the hemostatic material comprising oxidized derivatized esterified cellulose (e.g., a hemostatic fabric, sponge, puff, matrix, gel, or powder prepared as described above, bandage, tunicate, constrictive bandage, or another form) directly to the wound, in certain embodiments, it can be preferred to incorporate the hemostatic material into a wound dressing including other components.

To ensure that the hemostatic material remains affixed to the wound, a suitable adhesive can be employed, for example, along the edges or a side of the hemostatic fabric, sponge or puff. Although any adhesive suitable for forming a bond with skin or other tissue can be used, it is generally preferred to use a pressure sensitive adhesive. Pressure sensitive adhesives are generally defined as adhesives that adhere to a substrate when a light pressure is applied but leave little to no residue when removed. Pressure sensitive adhesives may include, but are not limited to, solvent in solution adhesives, hot melt adhesives, aqueous emulsion adhesives, calenderable adhesives, and radiation curable adhesives. Solution adhesives may be preferred for most uses because of their ease of application and versatility. Hot melt adhesives may typically be based on resin-tackified block copolymers. Aqueous emulsion adhesives may include those prepared using acrylic copolymers, butadiene styrene copolymers, and natural rubber latex. Radiation curable adhesives may typically consist of acrylic oligomers and monomers, which may cure to form a pressure sensitive adhesive upon exposure to ultraviolet lights.

The most commonly used elastomers in pressure sensitive adhesives may include natural rubbers, styrene-butadiene latexes, polyisobutylene, butyl rubbers, acrylics, and silicones. In preferred embodiments, acrylic polymer or silicone based pressure sensitive adhesives may be used. Acrylic polymers may often have a low level of allergenicity, be cleanly removable from skin, possess a low odor, and exhibit low rates of mechanical and chemical irritation. Medical grade silicone pressure sensitive adhesives may be preferred for their biocompatibility.

Amongst the factors that influence the suitability for a pressure sensitive adhesive for use in wound dressings of preferred embodiments is the absence of skin irritating components, sufficient cohesive strength such that the adhesive can be cleanly removed from the skin, ability to accommodate skin movement without excessive mechanical skin irritation, and good resistance to body fluids.

In preferred embodiments, the pressure sensitive adhesive may comprise a butyl acrylate. While butyl acrylate pressure sensitive adhesives may generally be preferred for many applications, any pressure sensitive adhesive suitable for bonding skin can be used. Such pressure sensitive adhesives are well known in the art.

As discussed above, the hemostatic materials of preferred embodiments generally exhibit good adherence to wounds such that an adhesive, for example, a pressure sensitive adhesive, is generally not necessary. However, for ease of use and to ensure that the hemostatic material remains in a fixed position after application to the wound, it can be preferable to employ a pressure sensitive adhesive.

While the hemostatic puffs, fabrics and other hemostatic materials comprising oxidized derivatized esterified cellulose may generally exhibit good mechanical strength and wound protection, in certain embodiments, it can be preferred to employ a backing or other material on one side of the hemostatic material. For example, a composite including two or more layers can be prepared, wherein one of the layers is the hemostatic material and another layer an elastomeric layer, gauze, vapor-permeable film, waterproof film, a woven or nonwoven fabric, a mesh, or the like. The layers can then be bonded using any suitable method (e.g., the application of adhesives, such as pressure sensitive adhesives, hot melt adhesives, curable adhesives; the application of heat or pressure, such as in lamination, a physical attachment through the use of stitching, studs, other fasteners; or the like).

Other components can be combined with the hemostatic materials for use in wound dressings as are known in the art, such as preservatives, stabilizers, dyes, buffers, alginate pastes or beads, hydrocolloid pastes or beads, hydrogel pastes or beads, as well as medicaments and other therapeutic agents as described above.

In other embodiments, the soluble hemostatic material comprising the described oxidized derivatized esterified cellulose may be mixed with any suitable liquid to produce a hemostatic gel. The gel may be used inside and outside the body.

The following examples may describe this invention in further detail, but these examples shall not be construed as limiting the scope of this invention.

EXAMPLE 1

As mentioned, the hemostatic material comprising the described oxidized derivatized esterified cellulose may be made in a variety of methods. Nevertheless, one non-limiting example of a preferred method for making the hemostatic material may comprise:

1) Activating Treatment:
   a) Placing two liters of sodium hydroxide, two liters of sodium carbonate, and one liter of sodium hypochlorite in to the internal bladder of a reaction vessel, then adding in an appropriate amount of pure water and stirring until the ingredients are totally dissolved and a pH value of about 8 to 9.5 is achieved. Then, pouring 60 liters of 95% ethyl alcohol in to the internal bladder and mix. Then turn on the stainless steel heater and keep the temperature of the internal bladder between about 25° C. and about 28° C. and hold for 10 hours.
   b) Put about 80 meters of clinical use gauze made from cellulose into the mixed solution in the reaction vessel. At this point, the temperature of the external body should be 30° C.±3° C. Additionally, the temperature of the internal bladder should be 26° C.±1° C.
   c) Decrease the temperature of the internal bladder to 20° C.±3° C., and begin to rotate the reaction vessel for about three to about five hours.
   d) Allow cold water from a refrigerator to move into the internal bladder with a temperature of 20° C.±3° C., after 30 minutes the temperature will drop to 5° C.±3° C. Allow this reaction to occur for one hour.

2) Oxidizing treatment
   a) Add about 60 liters of 95% ethyl alcohol and 12 bottles of chloroacetic acid into the reaction vessel. Then let in water with the temperature at about 45° C. After 30 minutes the temperature in the internal bladder may go up from 5° C.±3° C. to 41° C.±3° C. Add one bottle of hydrogen peroxide, decrease the temperature to 32° C.±3° C., and allow the reaction to continue for about 1.5 hours.

3) Rinsing and Drying Up
   a) Put the gauze form the reaction vessel into a stainless-steel tub, add in 60 kg 70% ethyl alcohol, stir and rise. Then dry the gauze up by centrifugal dewatering.
   b) Put the gauze obtained as above into another stainless-steel tub with 60 kg 70% ethyl alcohol; counteract it by adding into Hydrochloric acid to achieve the pH value of 7±0.5.
   c) Take out the gauze, dry it up, and treat the gauze one more time or many times as described above in another stainless-steel tub until the solution becomes clear. Then take out the gauze, dry it up, and make it flat by ironing.
   d) Dry the rinsed gauze up in a dryer. Turn on the power switch, press on the drying button, the dryer begins to run and removes the unwanted ethyl alcohol form the gauze.

4) Sterilizing and Ironing Out
   a) Take out the gauze from the dryer and insert one end thereof into the rollers for drying and ironing. The rolling of the rollers may make the gauze go through and as well as continue to dry up the gauze and iron out the gauze and so the gauze may comes out flat before being scrolled up.
   b) A test may then be completed by cutting a 2 $cm^2$ piece of gauze and dipping the gauze into a cup with water. In some embodiments, after 2-3 minutes, the gauze may appear to be viscous, and within 2 hours, the gauze may be dissolved in to a mixture with the water.

Having described these aspects of the invention, it is understood that the invention provides a new kinds of soluble hemostatic fabric material and it can be made in the industry simply and economically. It is also understood that the invention defined by the appended claims is not to be limited by particular details set forth in the above description, as many apparent variations thereof are possible without departing from the spirit or scope thereof.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A hemostatic material, comprising a polymer of oxidized derivatized esterified cellulose comprising a chain of monomers, each monomer having a structural formula of:

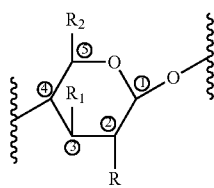

wherein, for a first plurality of the monomers in the chain:
R is —OCH$_2$(COO)CH$_2$CH$_3$,
R1 is —OCH$_2$(COO)CH$_2$CH$_3$, and
R2 is —CH$_2$OCH$_2$(COO)CH$_2$CH$_3$, and
wherein, for a second plurality of monomers in the chain:
R is —OCH$_2$(COO)CH$_2$CH$_3$,
R1 is —OCH$_2$(COO)CH$_2$CH$_3$, and
R2 is —(COO)CH$_2$CH$_3$.

2. The hemostatic material of claim 1, further comprising a therapeutic agent.

3. The hemostatic material of claim 2, wherein the therapeutic agent comprises an agent selected from a list consisting of: an anti-inflammatory agent, an anti-infective agent, an anesthetic, and a chemotherapy agent.

4. The hemostatic material of claim 1, further comprising: an adhesive on at least one side of the hemostatic material.

5. The hemostatic material of claim 1, wherein the hemostatic material is shaped into a sheet, towel, or sponge form.

6. The hemostatic material of claim 1, wherein the hemostatic material is a fabric.

7. The hemostatic material of claim 6, wherein the fabric is shaped into one or more strips that are sized for insertion into the human nose.

8. The hemostatic material of claim 7, wherein the fabric of one or more of the strips includes an extension for facilitating removal of the one or more strips from the human nose.

9. The hemostatic material of claim 1, wherein for a third plurality of the monomers in the chain:
R is —OCH$_2$(COO)CH$_2$CH$_3$ or —OH,
R1 is —OCH$_2$(COO)CH$_2$CH$_3$ or —OH, and
R2 is —CH$_2$OCH$_2$(COO)CH$_2$CH$_3$ or —(COO)CH$_2$CH$_3$.

10. The hemostatic material of claim 1, wherein for a third plurality of the monomers in the chain:
R is —OH,
R1 is —OCH$_2$(COO)CH$_2$CH$_3$ or —OH, and
R2 is —CH$_2$OCH$_2$(COO)CH$_2$CH$_3$ or —(COO)CH$_2$CH$_3$.

11. The hemostatic material of claim 1, wherein for a third plurality of the monomers in the chain:
R is —OCH$_2$(COO)CH$_2$CH$_3$ or —OH,
R1 is —OH, and
R2 is —CH$_2$OCH$_2$(COO)CH$_2$CH$_3$ or —(COO)CH$_2$CH$_3$.

* * * * *